United States Patent

Datta et al.

[11] Patent Number: 5,945,532
[45] Date of Patent: Aug. 31, 1999

[54] METHOD FOR MANUFACTURE OF CEPHALOSPORIN AND INTERMEDIATES THEREOF

[75] Inventors: Debashish Datta; Vinod George; Bishwa Prakash Rai, all of Mandideep, Dist. Raisen, M.P., India

[73] Assignee: Lupin Laboratories Limited, Bombay, India

[21] Appl. No.: 09/154,787

[22] Filed: Sep. 16, 1998

Related U.S. Application Data

[62] Division of application No. 08/624,737, Mar. 26, 1996, Pat. No. 5,739,346.

[30] Foreign Application Priority Data

Dec. 26, 1995 [IN] India .................. 545/BOM/95

[51] Int. Cl.$^6$ ................................... C07D 501/34
[52] U.S. Cl. .............. 540/227; 540/226; 540/222; 540/228; 548/194; 548/253; 548/254
[58] Field of Search ................. 540/227, 226, 540/222, 228; 548/194, 253, 254

[56] References Cited

U.S. PATENT DOCUMENTS

| | | | |
|---|---|---|---|
| 4,152,432 | 5/1979 | Heymes et al. | 424/246 |
| 5,037,988 | 8/1991 | Meseguer et al. | 548/194 |
| 5,317,099 | 5/1994 | Lee et al. | 540/222 |
| 5,663,331 | 9/1997 | Kim et al. | 540/227 |
| 5,716,626 | 2/1998 | Sakurai et al. | |
| 5,739,346 | 4/1998 | Datta et al. | 548/194 |

FOREIGN PATENT DOCUMENTS 0 037 380   9/1984   European Pat. Off. .

Primary Examiner—Mukund J. Shah
Assistant Examiner—Pqavanaram K Sripada
Attorney, Agent, or Firm—Merchant, Gould, Smith, Edell, Welter & Schmidt

[57] ABSTRACT

This invention relates to reactive derivatives of 2-(2-aminothiazol-4-yl)-2-methoxyimino acetic acid and 1H-tetrazol-1-acetic acid of the following general formula I,

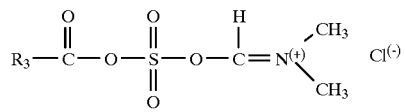

wherein

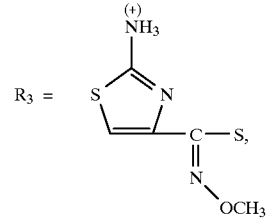

as well as to use thereof in the manufacture of cephalosporin antibiotics such as cefotaxime, ceftriaxone and cefazolin.

4 Claims, No Drawings

METHOD FOR MANUFACTURE OF CEPHALOSPORIN AND INTERMEDIATES THEREOF

This application is a Division of application Ser. No. 08/624,737, filed on Mar. 26, 1996, now patented as U.S. Pat. No. 5,739,346.

BACKGROUND OF THE INVENTION

1. Field of the Invention

This invention relates to reactive derivatives of 2-(2-aminothiazol-4-yl)-2-methoxyimino acetic acid and 1H-tetrazol-1-acetic acid of the following general formula I,

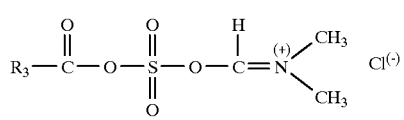

wherein

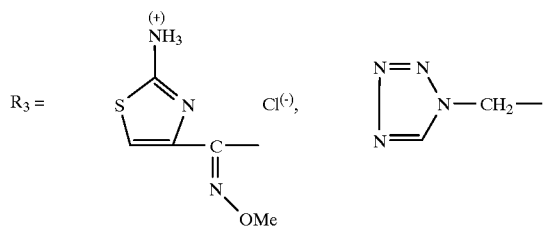

The present invention also relates to the process for the production thereof as well as to the process for the use thereof in the manufacture of cephalosporin antibiotics such as cefotaxime, ceftriaxone and cefazolin.

2. Discussion of the Background

It is known in the art to synthesize different cephalosporin antibiotics, for instance compounds of formula II which generally comprise of amidification of 7-position of appropriate cephalosporin nucleus with or without substitution at 3α-position, with the desired addenda.

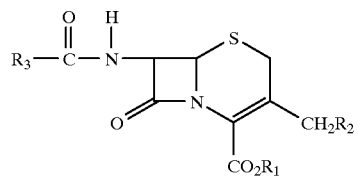

wherein $R_1$=H, carboxylic protecting group;

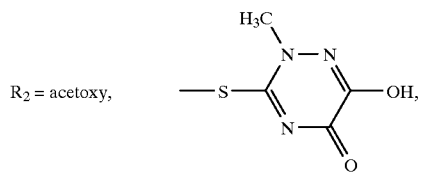

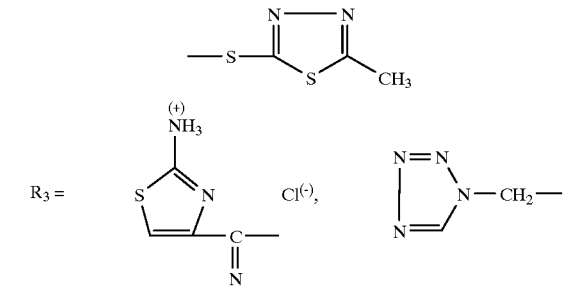

Usually, the synthesis by such known processes of various cephalosporin antibiotics comprises of acylation of 7-aminocephalosporanic acid (7-ACA) or 7-amino desacetoxycephalosporanic acid (7-ADCA) derivatives with a reactive derivative such as an acid chloride, an acid anhydride, an activated ester, etc., of the addendum acid for instance of formulas III and IV.

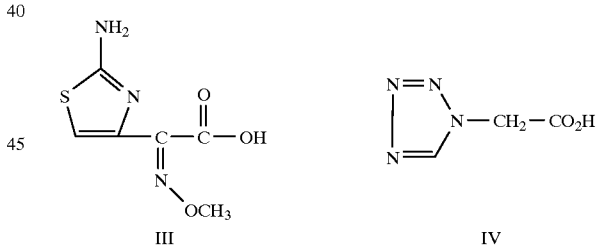

The above can be described schematically as follows:

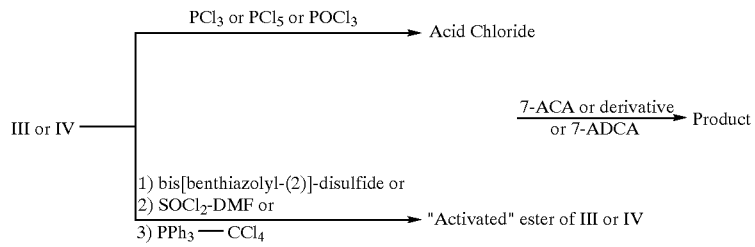

A number of methods utilizing this concept have been reported for the functionalization of position 7 of the desired cephalosporin nucleus and these are summarized below.

U.S. Pat. No. 4,152,432 describes acylation of 7-ACA with an acid chloride of formula V in which the amino group in the thiazole ring is protected. The amino group is subsequently deprotected generally by hydrolysis or hydrogenolysis.

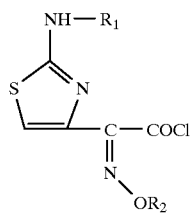

V

Because of the inherent inefficiency of amidification of the 7-amino group of cephalosporin nucleus and also of the steps involved in protection and deprotection of the amino group of the thiazolyl ring, the overall yields are low and far from satisfactory. JP 52-102096, JP 53-157596 and GB 2 025 933 utilize the same chemistry—i.e., formation of 2-(2-aminothiazol-4-yl)-2-oxyimino acetyl chloride either with $PCl_3$, $PCl_5$, $SOCl_2$ or $POCl_3$.

Needless to say, the protection and deprotection of the amino group of the thiazolyl ring are involved in such conventional synthesis techniques for cephalosporin antibiotics.

Besides protection and deprotection of the amino function, the resulting acid chloride, e.g., 2-(2-aminothiazol-4-yl)-2-methoxyimino acetyl chloride, 1H-tetrazol-1-acetyl. chloride, is unstable, creating further complication for the synthesis of the desired cephalosporin antibiotics.

U.S. Pat. No. 3,954,745 utilizes the same concept, i.e., formation of 1H-tetrazol-1-acetyl chloride in dimethylacetamide and coupling the acid chloride with the DMF-solvate of the hydrochloride of 7-aminocephalosporin of the following formula VI as shown below to yield cefazolin.

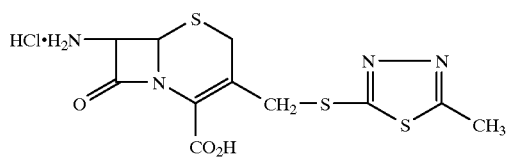

VI

However, yields are low. Also, the acylating agent, 1H-tetrazol-1-acetyl chloride, because of its inherent instability, is difficult to isolate and store at room temperature. Another limitation of this process is that acylation is to be carried out in strictly anhydrous conditions.

U.S. Pat. No. 5,317,099 describes a process for the synthesis of β-lactam derivatives such as cefotaxime and ceftriaxone in which silylated 7-ACA is acylated with acyloxyphosphonium chloride derivative of 2-(2-aminothiazol-4-yl)-2-syn-methoxyimino acetic acid, which, in turn, is prepared from triphenyl phosphine (TPP), hexachloroethane or carbontetrachloride and 2(2-aminothiazol-4-yl)-2-syn-methoxyimino acetic acid. Since triphenyl phosphine (TPP) is used as a reactant, the overall cost of coupling the addendum III to the cephalosporin nucleus becomes high.

EP 037,380 describes a process for the synthesis of cephalosporin antibiotics, e.g., cefotaxime and ceftriaxone, which comprises acylation of 7-ACA derivatives with an intermediate of formula VII,

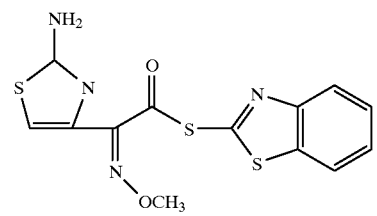

VII

However, the synthesis of the 2-(2-aminothiazol-4-yl)-2-methoxyimino acetic acid benzthiazolyl thioester from 2-(2-aminothiazol-4-yl)-2-methoxyimino acetic acid and bis [benzthiazolyl-(2)]disulfide, involves the use of a costly condensation aid such as triphenyl phosphine (TPP), rendering the whole synthesis very costly.

U.S. Pat. No. 5,037,988 describes a process for the production of cephalosporins, in particular, cefotaxime and ceftriaxone, in which an activated form of an organic acid, i.e., 2-(2-aminothiazol-4-yl)-2-oxyiminoacetylsulfite dialkylformiminium halide hydrohalide of the following formula VIII;

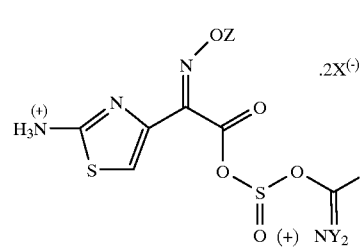

VIII

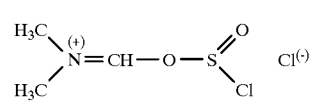

IX is coupled with a 7-aminocephalosporanic acid derivative. The compound of formula VIII was prepared by reacting 2-(2-aminothiazol-4-yl)-2-oximino acetic acid with dimethyl formiminium chloride chlorosulfite of formula IX, which in turn was prepared by reacting approximately equimolar quantities of thionyl chloride and dimethylformamide at room temperature in specific solvents only like benzene or toluene, and hence suffers from a limitation.

However, poor results have been obtained when an attempt was made to prepare the compound of formula IX in solvents such as chloroform and dichloromethane. In these solvents, the compound IX did not separate out in its characteristic form of insoluble oil, as the polarity of these solvents does not allow the formation of these reactants.

Thus, it is evident that the procedures described in the prior art for the preparation of 7-acylamino cephalosporanic acid derivatives are either complex, involving protection or deprotection, or costly, or have other limitations.

SUMMARY OF THE INVENTION

It is thus the primary objective of the present invention to provide reactive derivatives of general formula 1 which would be suitable for use in the manufacture of cephalosporin antibiotics and would not be subject to the above complexities in the manufacture of cephalosporin antibiotics.

Another object of the present invention is directed to provide a process for the synthesis of the reactive derivatives of 2-(2-aminothiazol-4-yl)-2-methoxyimino acetic acid(III) and 1H-tetrazol-1-acetic acid(IV) of general formula I, which would be simple to manufacture.

Yet a further objective of the present invention is to provide a process for the synthesis of cephalosporin antibiotics such as cefotaxime, ceftriaxone and cefazolin, which would avoid the protection and deprotection of the amino group of the thiazolyl ring reported in the known art.

Another further object of the present invention is to provide a process for the synthesis of cephalosporin antibiotics of the type mentioned above which would be simple to carry out and will be cost-effective.

Yet another further object of the present invention is to provide for the synthesis of cephalosporin antibiotics of the type mentioned above which would favor better and consistent yield of cephalosporin antibiotics with desired characteristics for use as an antibiotic.

Thus, according to one aspect of the present invention, compounds of formula I are produced by a process comprising reacting dimethyl formiminium chloride chlorosulphate (DFCCS) of formula XI with 2-(2-aminothiazol-4-yl)-2-methoxyimino acetic acid(III) or 1H-tetrazol-1-acetic acid (IV) in a solvent such as dichloromethane at a temperature ranging from −30° C. to 15° C. to yield the compound of formula I.

In the instance in formula I

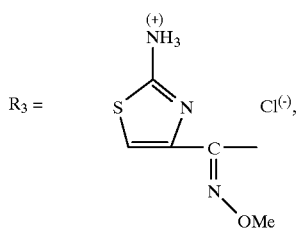

the above reactive derivative of formula I is a reactive derivative of 2-(2-aminothiazol-4-yl)-2-methoxyimino acetic acid of formula Ia,

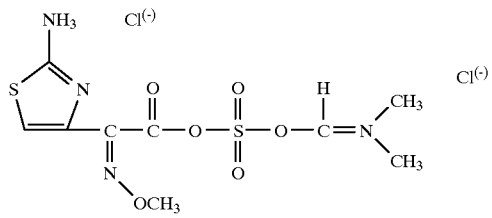

Further, in the instance in formula I,

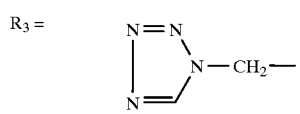

the above reactive derivative of formula I is a reactive derivative of 1H-tetrazol-1-acetic acid of formula Ib,

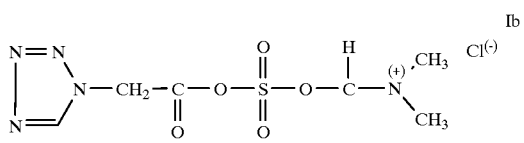

In accordance with a further aspect of the invention, there is provided a process for the preparation of the desired cephalosporin antibiotics which comprises reacting silylated 7-aminocephalosporanic acid derivatives of formula X,

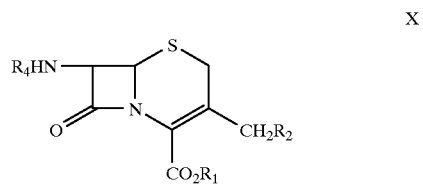

in which $R_1$=carboxylic protecting group or hydrogen
$R_2$=acetoxy,
$R_4$=silyl group or hydrogen
with a reactive derivative of 2-(2-aminothiazol-4-yl)-2-methoxyimino acetic acid of formula Ia or 1H-tetrazol-1-acetic acid of formula Ib, in dichloromethane at a temperature ranging from −70° C. to −50° C.

DETAILED DESCRIPTION OF THE INVENTION

Thus, in accordance with the invention, compounds of formula Ia and Ib are prepared by reacting N, N-dimethyl formiminium chloride chlorosulphate (DFCCS) of formula XI, with 2-(2-aminothiazol-4-yl)-2-methoxyimino acetic acid (III) or IH-tetrazol-1-acetic acid (IV).

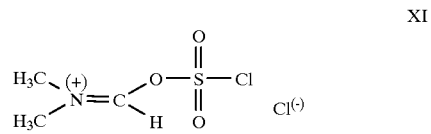

DFCCS(XI) is a known compound and described in the literature viz Z. Chem, 6(4), 148 (1966), J. C. S. Perkin Trans I, 2004–2007 (1972); Bull Chem Soc Jpn, 58, 1063–1064; Adv.-Org. Chem. 9(2), 5, (1979); Synthetic Reagents Vol. 4, 388–389; Angew Chem Internal Edit, 1(12), 647 (1962).

While DFCCS(XI) prepared by any known process might be used, the inventors have found that best results are obtained when DFCCS(XI) is prepared by the following process.

The preferred process of obtaining the DFCCS(XI) comprises adding sulfuryl chloride to dimethylformamide at −20° C. The temperature is raised to 0° C. at which the solid adduct crystallized out, which is vigorously stirred for one hour, followed by addition of dichloromethane to the resulting reaction mixture. The temperature was raised to 15° C.–20° C. and at this temperature the solid crystals melt, resulting in the formation of an immiscible layer of the desired adduct, i.e., XI.

Such mode of preparation of DFCCS(XI) is illustrated in the following scheme A:

Scheme A

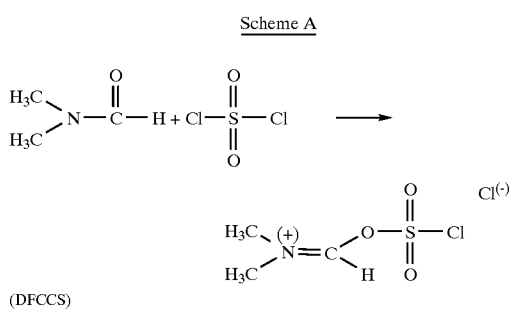

(DFCCS)

The DFCCS(XI) adduct thus obtained by the preferred process of the invention is found to be advantageous in use in the process of manufacture of the reactive derivatives of formula X in accordance with the objective of the invention for the reasons given below.

i) Unlike the complex IX used in the prior art, DFCCS (XI) used in the process of the present invention remains stable and does not get converted to the normal Vilsmeier's reagent. It has been observed that DFCCS (XI) of the present invention is apparently more stable than DFCS(IX) described in U.S. Pat. No. 5,037,988. In particular, it is found that the thus obtained DFCCS (XI) used in the process of the invention is distinct from thionyl chloride-DMF adduct, i.e., dimethylformiminium chloride chlorosulfite(IX) known in the art. The melting point of the latter is 138°–140° C. [Helv. Chim Acta, 62, 1655 (1959)] while that of the DFCCS adduct(XI) is 40° C.–41° C. [Z. Chem 6(4), 148 (1966)].

ii) The DFCCS(XI) used in the process of the invention can be prepared in any solvent such as benzene, toluene, acetonitrile or dichloromethane, and preferably in the absence of solvents. This is advantageous and clearly distinct from the thionyl chloride—DMF adduct, i.e., dimethylformiminium chloride chlorosulfite described in U.S. Pat. No. 5,037,988, which cannot be prepared in solvents such as chloroform or dichloromethane, since these solvents facilitate complete or partial conversion of dimethyl formiminium chloride chlorosulfite to normal Vilsmeier's reagent.

iii) It has been found that sulfuryl/DMF adduct DFCCS of formula XI is more stable than DFCS adduct of formula IX made from thionyl chloride and DMF. Thus, when DFCCS(XI) adduct was kept at ambient temperature for 16 hours and used for further complexation with compounds of formula III and IV for synthesis of the activated ester required for the final acylation reaction, the drop in yield in the final antibiotic was about 26% (85% when used fresh and 59% after storage of DFCCS for 16 hours). Similarly, when DFCS adduct was kept at ambient temperature for 16 hours and further processed for synthesis of the final antibiotic, the drop in yield was about 35% (80% when used fresh and 45% when used after 16 hours). Hence, DFCCS adduct of formula XI obtained by the preferred process described above has superior stability compared to DFCS adduct of formula IX and this is a great advantage for cost-effective manufacture of cephalosporin antibiotic like Cefotaxime, Ceftriaxone and Cefazolin.

Thus, the use of DFCCS(XI) for synthesis of the compound of formula Ia or Ib, the activated ester of compounds of formula III and IV, provides a practical, cost-effective and safe method for manufacture of the desired cephalosporin antibiotics like cefotaxime, ceftriaxone and cefazolin.

The process of manufacture of the desired cephalosporin antibiotic according to the improved process of the invention basically involves the following:

In Step I, the 2-(2-aminothiazol-4-yl)-2-synmethoxyimino acetic acid(III) was activated with N,N-dimethylformiminium chloride chlorosulphate(XI) in dichloromethane at a temperate ranging from –30° C. to –15° C. to yield reactive form Ia.

In Step II, the reactive form Ia was treated with silylated 7-aminocephalosporanic acid (X) at a temperature ranging from –70° C. to –30° C., preferably –55° C., to yield the desired cephalosporins such as cefotaxime, ceftriaxone.

The use of conventional silylating agents such as hexamethyldisilazane, trimethylchlorosilane, bis (trimethyl) silylacetamide is considered to be appropriate for silylation of 7-ACA. Alternatively, 7-amino-cephalosporanic acid can also be used in the form of its quaternary salt with tetramethyl guanidine.

The basic compounds used as acid scavenging agent to capture HCl released during silylation include N,N-dimethylaniline, diethylamine, pyridine, preferably N,N-dimethylaniline.

The process of the present invention described above may be represented in scheme B:

Scheme B

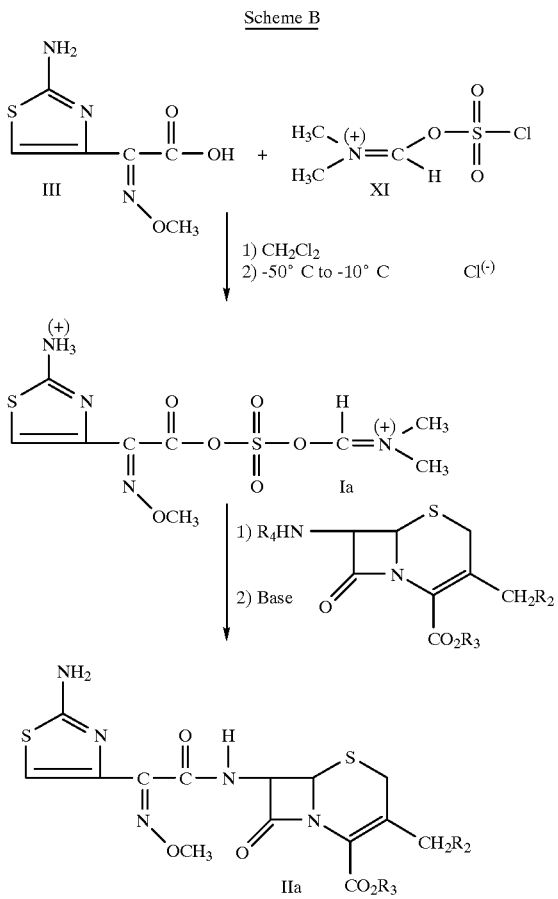

Cefazolin is prepared from 7-amino-3-(2-methyl-1,3,4-thiadiazol-5-yl)thiomethyl-3-cephem-4-carboxylic acid and reactive derivative of 1H-tetrazol-1-acetic acid of formula Ib in a manner similar to that described for the preparation of cefotaxime, ceftriaxone.

The preparation of cefazolin is illustrated in the following scheme C:

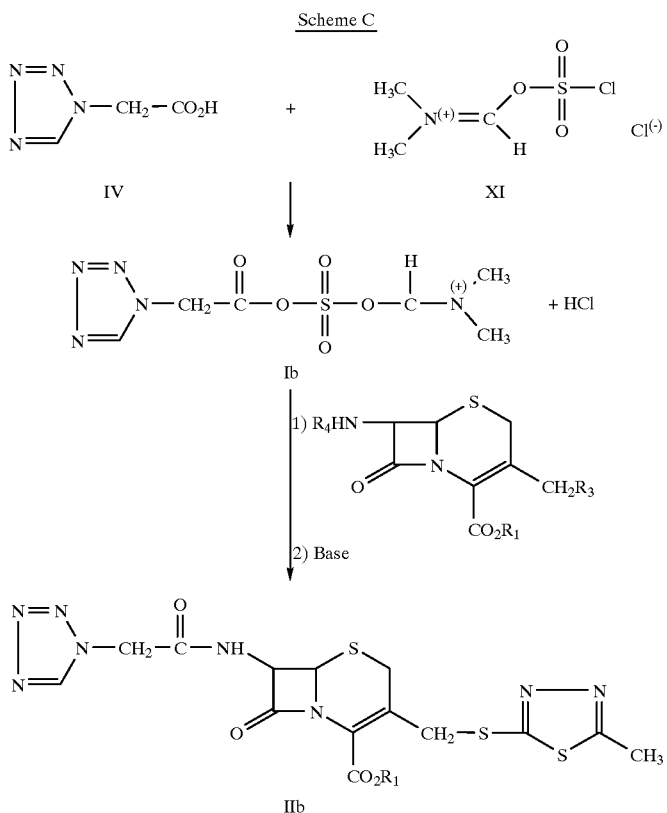

The process of the invention, its objects and advantages will be further apparent from the non limiting examples illustrated hereunder.

EXAMPLES

Example 1

Preparation of 7-[(2-(2-aminothiazol-4-yl)-2-syn-methoxyimino)acetamido] cephalosporanic acid (cefotaxime)

A) Activation of the 2-(2-aminothiazol-4-yl)-2-syn-methoxyimino acetic acid.

11.9 g of sulfuryl chloride was added dropwise to 6.4 g of dimethlyformamide at $-20°$ C. The temperature was slowly raised to $0°$ C. at which the solid adduct crystallized out. This was stirred vigorously for 1 hour and 50 ml of dichloromethane was added to the solid crystals. The temperature was raised to $15°-20°$ C. and at this temperature the crystallized adduct melted and formed an immiscible layer with dichloromethane. The lower portion (N,N-dimethyl forminium chloride chlorosulphate) was added to a pre cooled slurry of 16.02 g of 2-(2-aminothiazol-4-yl)-2-syn-methoxyimino acetic acid in 150 ml of dichloromethane at $-20°$ C. to get a clear solution, which was kept for 1 hour at this temperature.

B) Preparation of 7-amino cephalosporanic acid solution.

20.0 g of 7-aminocephalosporanic acid was taken in 150 ml of dichloromethane and 12.42 g of hexamethyldisilazane was added to it, followed by refluxing for two hours. The clear solution obtained was cooled to $10°$ C. and 12.1 ml of dimethylaniline was added to it, followed by cooling to $-55°$ C.

C) Acylation

The reaction mixture (A) was cooled to $-55°$ C. and the reaction mixture (B) was added to it to get a clear solution. The temperature was maintained at $-55°$ C. for 10 minutes. The quantification of the condensed mass showed the formation of 82.5% of cefotaxime acid. PMR (DMSO-$d_6$)$\delta$ ppm: 2.00(s), 3.3(q), 3.8(s), 4.9(q), 4.97(q), 5.60(2d), 6.70 (s), 7.2(bs), 9.47(d).

D) Isolation of 7-[(2-(2-aminothiazol-4-yl)-2-syn-methoxyimino)acetamido] cephalosporanic acid.

200 ml of water was added to the above condensed mass and the temperature was brought to $25°$ C. in 20 minutes. At this temperature, the pH of the hydrolyzed mass was brought to 6.5 by using triethylamine. The aqueous layer was taken and 40 ml of 85% formic acid was added at $30°$ C. The product in the formic acid solvate form started precipitating after 10 minutes. This was cooled to $5°$ C. and was stirred for one hour and then filtered to yield 29 g (87%) of the formic acid solvate with a purity of 92%.

UV max=233.0 nm (in water)

E) Conversion of formic acid solvate to isopropyl alcohol solvate of cefotaxime:

The above formic acid solvate was taken in 175 ml of isopropyl alcohol and heated to $50°$ C. for 4–5 hours. The isopropyl alcohol solvate thus formed was cooled to $5°$ C. and then filtered to yield 26.97 g (81%) of the isopropyl alcohol solvate with a purity of 92%. MP=202–205° C.

a) IR: (main bands) in $cm^{-1}$.

3420 (—$NH_2$), 3340 (—NH, —$NH_2$), 1760 (—C=O lactam), 1730 (—C=C, carboxylic, 1650 (—C(=O—NH), 1385–1355 (—O—CO—$CH_3$).

b) UV Characteristics: UV max=235.5 nm (in water), E(1%, 1 cm)=376.00 c) Specific rotation: $[\alpha]^{20}_D=+61.232$ (C=1% aqueous solution)

F) Conversion of Isopropyl alcohol solvate of cefotaxime to cefotaxime sodium:

10.0 g of the above solvate was taken in 60 ml of methanol and 11 ml of water and the mixture was cooled to +5° C. To this was slowly added 1.8 g of sodium acetate dissolved in 20 ml methanol to get a clear solution. To the above solution 400 ml of isopropyl alcohol was added within one hour to get cefotaxime sodium in the crystal form.

Example 2

Preparation of 7-[(2-(2-aminothiazol-4-yl)-2-syn-methoxyimino) acetamido] cephalosporanic acid (cefotaxime)

Same procedure as in example 1 was followed, but 400 ml of dichloromethane was used for the activation of 2-(2-amino thiazol-4-yl)-2-syn-methoxyimino acetic acid. Cefotaxime was prepared in 81.4% yield.

Example 3

Preparation of 7-[(2-(2-aminothiazol-4-yl)-2-syn-methoxyimino) acetamido] cephalosporanic acid (cefotaxime)

A) Activation of 2-(2-aminothiazol-4-yl)-2-syn-methoxyimino acetic acid:
Same procedure as in example 1 was followed.
B) Preparation of 7-aminocephalosporanic acid solution:
Same procedure as in example 1 was followed.
C) Acylation:
The reaction mixture (A) was cooled to −70° C. and reaction mixture (B) was added to it to get a clear solution. The temperature of the condensed mass was maintained at −70° C. for 10–15 minutes. The quantification of the condensed mass showed the formation of 75.5% of cefotaxime.
D) Isolation of 7-[(2-(2-aminothiazol-4-yl)-2-syn-methoxyimino)acetamido] cephalosporanic acid:
Same procedure as in example 1 was followed.

Example 4

Preparation of 7-[(2-(2-aminothiazol-4-yl)-2-syn-methoxyimino)acetamido] cephalosporanic acid (cefotaxime)

A) Activation of 2-(2-aminothiazol-4-yl)-2-syn-methoxyimino acetic acid.
19.8 g of sulfuryl chloride was added dropwise to 10.7 g of dimethylformamide at −20° C. The temperature was slowly raised to 0° C. at which white solid crystallizes out. The reaction mixture was stirred vigorously for one hour. 60 ml of dichloromethane was added to the solid crystals and the temperature was brought to 15°–30° C. At this temperature, the solid crystals melted to form immiscible layer. The lower layer was added to a pre-cooled slurry of 15.08 g of 2-(2-aminothiazol-4-yl)-2-syn-methoxyimino acetic acid in 120 ml of dichloromethane at −20° C. to get a clear solution which was kept for one hour at this temperature.
B) Preparation of 7-aminocephalosporanic acid solution:
Same procedure as in example 1 was followed.
C) Acylation:
The reaction mixture A was cooled to −55° C. and the reaction mixture B was added to it to get a clear solution. The temperature was maintained at −50° C. for 10 minutes. The quantification of the condensed mass showed only 36.3% of cefotaxime.
D) Isolation of 7-[(2-(2-aminothiazol-4-yl)-2-syn-methoxyimino)acetamido] cephalosporanic acid:
Same procedure as in example 1 was followed.

Example 5

Preparation of 7-[(2-(2-aminothiazol-4-yl(-2-syn-methoxyimino)acetamido] cephalosporanic acid (cefotaxime)

A) Activation of 2-(2-aminothiazol-4-yl)-2-syn-methoxyimino acetic acid:
10.9 g of sulfuryl chloride was added dropwise to 5.9 g of dimethylformamide at −20° C. The temperature was slowly increased to 0° C. at which the solid adduct crystallized out. This was vigorously stirred for one hour at this temperature. To the solid crystals, 30 ml of dichloromethane was added and the temperature was raised to 15°–20° C. At this temperature the solid crystals melted and formed an immiscible layer with dichloromethane. The lower layer was added to pre-cooled slurry of 15.08 g of 2-(2-aminothiazol-4-yl)-2-syn-methoxyimino acetic acid in 120 ml of dichloromethane at −20° C. to get a clear solution which was kept for one hour at the same temperature.
B) Preparation of 7-amino cephalosporanic acid solution:
Same procedure as in example 1 was followed.
C) Acylation:
The reaction mixture A was cooled to −55° C. and reaction mixture B was added to it to get a clear solution. The temperature of the condensed mass was kept at −50° C. for 10 minutes. The quantification of the condensed mass showed 60% of cefotaxime.
D) Isolation of 7-[(2-(2-aminothiazol-4-yl)-2-syn-methoxyimino)acetamido]cephalosporanic acid:
Same procedure as in example 1 was followed.

Example 6

Preparation of 7-[(2-(2-aminothiazol-4-yl)-2-syn-methoxyimino)acetamido]cephalosporanic acid (cefotaxime)

A) Activation of 2-(2-aminothiazol-4-yl)-2-syn-methoxyimino)acetic acid.
Same procedure as in example 1 was followed.
B) Preparation of 7-amino cephalosporanic acid solution:
Same procedure as in example 1 was followed.
C) Acylation:
The reaction mixture A was cooled to −55° C. and the reaction mixture B was added to it to get a clear solution. The temperature was maintained at −50° C. for 30 minutes instead of 10 minutes. The quantification of the condensed mass showed 55% of cefotaxime.
D) Isolation of 7-[(2-(2-aminothiazol-4-yl)-2-syn-methoxyimino)acetamido]cephalosporanic acid:
Same procedure as in example 1 was followed.

Example 7

Preparation of 7-[(2-(2-aminothiazol-4-yl)-2-syn-methoxyimino)acetamido] cephalosporanic acid (Cefotaxime)

A) Activation of 2-(2-aminothiazol-4-yl)-2-syn-methoxyimino acetic acid.
Same procedure as in example 1 was followed.
B) Preparation of 7-aminocephalosporanic acid solution:
20.0 g of 7-aminocephalosporanic acid was taken in 150 ml of dichloromethane and 12.24 g of hexamethyldisilazane was added to it followed by refluxing for 2 hours. The clear solution obtained was cooled to 10° C. and 9.4 g of acetamide was added to it followed by cooling to −55° C.

C) Acylation:

Same procedure as in example 1 was followed. Quantification of the condensed mass showed 60% of cefotaxime.

D) Isolation of 7-[(2-(2-aminothiazol-4-yl)-2-syn-methoxyimino)acetamido] cephalosporanic acid:

Same procedure as in example 1 was followed.

Example 8

Preparation of 7-[(2-(2-aminothiazol-4-yl)-2-syn-methoxyimino acetamido) cephalosporanic acid (cefotaxime)

A) Activation of 2-(2-aminothiazol-4-yl)-2-syn-methoxyimino acetic acid.

11.9 g of sulfuryl chloride was added dropwise to 6.4 g of dimethylformamide at −20° C. The temperature was slowly raised to 0° C. at which the solid adduct crystallizes out. This was stirred vigorously for one hour and 50 ml of dichloromethane was added to the solid crystals. The temperature was raised to 15–20° C. and at this temperature, the crystallized adduct melts and forms an immiscible layer with dichloromethane. The lower portion (N,N-dimethyl forminium chloride chloro sulphate) was added to a pre-cooled slurry of 16.25 g of 2-(2-aminothiazol-4-yl)-2-syn-methoxyimino acetic acid in 150 ml of dichloromethane at −20° C. to get a clear solution, which was kept for one hour at this temperature.

B) Preparation of 7-amino cephalosporanic acid solution:

20.0 g of 7-amino cephalosporanic acid was taken in 120 ml of $CH_2Cl_2$ and 10.65 gm hexamethyl disilazane and 0.1 gm imidazole was added to it. Start refluxing for 4.0 hours under $N_2$ atmosphere. (After 30 minutes to refluxing, clear solution obtained.) Cooled to 10° C. and 12.1 ml dimethyl aniline was added followed by cooling to 55° C.

C) Acylation:

The reaction mixture A was cooled to −55° C. and the reaction mixture B was added to it to get a clear solution. The temperature was maintained at −55° C. for 10 minutes. The quantification of the condensed mass showed the formation of 90–95% of cefotaxime acid depending on the potency of the starting product (7-ACA).

D) Isolation of 7-((2-(2-aminothiazol-4-yl)-2-syn-methoxyimino)acetamido]cephalosporanic acid:

80 ml of water was added to the above condensed mass and the temperature was brought to 25° C. in 20 minutes. At this temperature, the pH of the hydrolyzed mass was brought to 6.5 by using triethylamine. The aqueous layer separated. Organic layer was extracted with 20×2 ml DM Water. Combined aqueous layer and extraction was taken and 40 ml of 85% formic acid was added at 30° C. The product in the formic acid solvate form starts precipitating after 10 minutes. This was cooled to 0–5° C. and was stirred for one hour and then filtered to yield 30 gm (87%) of the formic acid solvate with a purity of 92%.

E) Conversion of formic acid solvate to isopropyl alcohol solvate of cefotaxime:

Same procedure as in example 1 was followed.

F) Conversion of isopropyl alcohol solvate of cefotaxime to cefotaxime sodium.

Same procedure as in example 1 was followed.

Example 9

Preparation of 7-(1-(1H)-tetrazolylacetamido)-3-[2-(5-methyl-1,3,4-thiadiazolyl)thiomethyl]-3-cephem-4-carboxylic acid (Cefazolin)

A) Activation of 1H-tetrazol-1-acetic acid:

9.41 g of sulfuryl chloride was added dropwise to 5.09 g of dimethylformamide at −20° C. The temperature was slowly raised to 0° C. at which the solid adduct crystallized out. To this 50 ml of dichloromethane was added and the solid crystals melted to form an immiscible layer. The lower layer was added to 8.9 g of 1H-tetrazol-1-acetic acid in 120 ml of dichloromethane at −20° C. The temperature was raised to 0° C. which resulted in the formation of a turbid reaction mass. This reaction mass was kept at 0° C. for one hour.

B) Preparation of 7-amino-3-[2-(5-methyl-1,3,4-thiadiazolyl)thiomethyl]-3-cephem-4carboxylic acid solution:

20.0 g of 7-amino-3-[2-(5-methyl-1,3,4-thiadiazolyl) thiomethyl]-3-cephem-4-carboxylic acid was taken in 120 ml dichloromethane and to this 9.39 g of hexamethyl disilazane was added and refluxed for two hours to get a clear solution. After two hours, the clear solution was cooled to 10° C. and 12.6 g dimethylaniline was added to it and the reaction mixture was further cooled to −40° C.

C) Acylation:

The reaction mixture A was cooled to −40° C., to which reaction mixture B was added and the temperature of the condensed mass was maintained at −25° C. for 10–15 minutes. The quantification of condensed mass showed 53% of cefazolin.

PMR(DMSO-$d_6$) δ ppm: 2.7(s,3H), 3.7(dd,2H), 4.35(dd, 2H), 5.15(d,1H), 5.4(s,2H), 5.8(q,1H), 9.39(s,1H), 9.6(d, 2H).

D) Isolation of 7-(1(1H)-tetrazolylacetamido)-3-[2-(5-methyl-1,3,4-thiadiazolyl)thiomethyl]-3-cephem-4-carboxylic acid.

To the above condensed mass, 100 ml of water was added and the pH was brought to 6 by using triethylamine. The layer was separated and the pH of the aqueous layer was adjusted to 1.5 to yield white crystals of cefazolin. This was filtered and washed with water, followed by methanol.

a) IR: (Main bands) in $cm^{-1}$
3280 (—NH), 3140, 3075 (N=N, —C=N— tetrazole ring), 2620, 2580 (—OH, bonded, —COOH), 1770 (C=O lactam), 1715 (C=O acid), 1670 (C=Q amide-I), 1555 (C=O amide-II).

b) UV Characteristics: UV max=272.5 nm (in water), E(1%, 1 cm)=290.76 c) Specific Rotation: $[\alpha]^{20}_D$=−19.6· (C=1% aqueous solution)

Example 10

Preparation of 7-(1-(1H)=tetrazolylacetamido)-3-[2-(5-methyl-1,3,4-thiadiazolyl)thiomethyl]-3-cephem-4-carboxylic acid A) Activation of 1H-tetrazol-1-acetic acid.

Same procedure as in example 8 was followed. But 140 ml of dichloromethane was used for activation.

B) Preparation of 7-amino-3-[2-(5-methyl-1,3,4-thiadiazolyl)thiomethyl]-3-cephem-4-carboxylic acid solution:

20.0 g of 7-amino-3-(2-methyl-1,3,4-thiadiazol-5-yl) thiomethyl-3-cephem-4-carboxylic acid was taken in 140 ml dichloromethane and hexamethyldisilazane was added and refluxed for two hours to get a clear solution. This solution was cooled to 10° C. and 12.6 g of dimethylaniline was added. The resulting mixture was cooled to −40° C.

C) Acylation:

The reaction mixture A was cooled to −40° C. to which reaction mixture B was added and the temperature of the resulting condensed mass was maintained at −25° C. for 10–15 minutes. The quantification of the condensed mass showed 61% of cefazolin.

D) Isolation of 7-(1-(1H)-tetrazolylacetamido)-3-[2-(5-methyl-1,3,4-thiadiazolyl)thiomethyl]-3-cephem-4-carboxylic acid.

Same procedure as in example 9 was followed.

Example 11

Preparation of 7-(((2-aminothiazol-4-yl)(methoxyimino)acetyl)amino)-8-oxo-3-(((1,2,5,6-tetrahydro-2-methyl-5,6-dioxo-1,2,4-triazin-3-yl)thio)methyl)-5-thia-1-azabicyclo (4.2.0)oct-2-ene-carboxylic acid )ceftriaxone):

A) Activation of 2-(2-aminothiazol-4-yl)-2-syn-methoxyimino acetic acid:

9.06 g of sulfuryl chloride was slowly added to 4.91 g of dimethylformamide at −25° C. The temperature was slowly raised to 0° C. in 60–90 minutes. At this temperature, white solid, i.e., dimethyl forminium chloride chlorosulfate (DFCCS), crystallizes out, 50 ml of dichloromethane was added to the solid crystals and stirred vigorously for 15–20 minutes when the solid crystals melt to form an immiscible white crystalline colored oil. The immiscible oil was decanted in the lower portion and was slowly added to 11.37 g of 2-(2-aminothiazol-4-yl) methoxyimino acetic acid in 120 ml of dichloromethane cooled to −30° C. in 20–30 minutes. The temperature was slowly raised to −10° C. in one hour to get a clear solution.

B) 7-amino-3-desacetoxy-3-((2,5-dihydro-6-hydroxy-3-methyl-5-oxo-as-triazin-3-yl) thio) cephalosporanic acid solution:

20.0 g of 7-amino-3-desacetoxy-3-((2,5-dihydro-6-hydroxy-3-methyl-5-oxo-as-triazin-3-yl)thio) cephalosporanic acid in 160 ml of dichloromethane. To the resulting reaction mixture 40 ml of N,O-bis-silyl acetamide was added and stirred for eight hours at 30° C. to get a clear solution, cooled at −20° C. and 8.35 ml dimethylaniline was added to it and the reaction mixture was finally cooled to −50° C.

C) Acylation:

The reaction mixture A was cooled to −30° C. and added to the reaction mixture B. The temperature was maintained at −40° C. for 20–30 minutes.

Thick precipitation occurred which became thin during stirring, HPLC showed the formation of 70% of ceftriaxone.

PMR (DMSO-d$_6$) δ ppm: 3.3(d), 3.59(s), 3.9(s), 4.2(d), 5.1(d), 5.72(d), 6.8(s), 9.7(d).

D) Isolation: After 30 minutes of the reaction, 200 ml of water was added at −40° C. and stirred for 30 minutes at 20–25° C. The pH of the reaction mass was brought to 6.5 by adding triethylamine. The aqueous layer was separated and was treated with 5.0 g of activated carbon and 2.0 g of sodium bisulfate for 30 minutes, filtered and washed with 40 ml of water. The pH is then adjusted to 3.2 by 1:1 HCl, seeded and the resulting mixture was stirred for 30 minutes and then further stirred for two hours at 0° C. to −5° C. The product was filtered, washed with chilled isopropyl alcohol to give 21 g (70%) of Ceftriaxone, Assay=92.88%–95%.

Example 12

Preparation of 7-[[(2-aminothiazol-4-yl)-2-syn-methoxyimino]acetamido]-8-oxo-3-[(1,2,5,6-tetrahydro-2-methyl-5,6-dioxo(-1,2,4 triazin-3-yl) thiomethyl cephalosporamic acid(ceftriaxone)

A) Activation of 2-(2-aminothiazol-4-yl)-2-syn-methoxyimino acetic acid.

Same procedure as in example 11 was followed.

B) Quaternary salt of 7-amino-3-desacetoxy-3-(2,5-dihydro-6-hydroxy-3-methyl-5-oxo-as-triazin-3-yl)thio) cephalosporin acid.

20.0 g of 7-amino-3-desacetoxy-3-(2,5-dihydro-6-hydroxy-3-methyl-5-oxo-as-triazin-3-yl)thio) cephalosporanic acid in 120 ml of dichloromethane was cooled to −15° C. and 12.3 g of tetramethyl guanidine (TMG) was added to it. The temperature was slowly raised to −20° C. to −25° C. in one hour. The reaction mixture was stirred for one hour at 25° C. to get a clear solution. This solution was further cooled to −30° C. to −35° C. and 8.35 ml dimethylaniline was added to it and the reaction mixture was finally cooled to −40° C.

C) Acylation:

Same procedure as in example 11 was followed. HPLC showed formation of 75% of ceftriaxone.

D) Isolation:

Same procedure as in example 11 was followed.

Example 13

Preparation of 7-[(2-aminothiazol-4-yl)(methoxyimino) acetamido]-8-oxo-3-[[(1,2,5,6-tetrahydro-2-methyl-5,6-dioxo-1,2,4-triazin-3-yl)thio]methyl] cephalosporanic acid (ceftriaxone)

A) Activation of 2-(2-aminothiazol-4-yl)-2-syn-methoxyimino acetic acid.

Same procedure as in example 11 was followed.

B) 7-amino-3-desacetoxy-3-[(2,5-dihydro-6-hydroxy-3-methyl-5-oxo-as-triazin-3-yl)thio]cephalosporanic acid solution.

20.0 g of 7-amino-3-desacetoxy-3-(2,5-dihydro-6-hydroxy-2-methyl-5-oxo-as-triazin-3-yl)thio) cephalosporanic acid in 200 ml of dichloromethane was taken and 19.05 g of trimethylsilyl chloride (TMCS) was added to it, followed by refluxing for three hours to give clear solution, cooled to −20° C. and 8.53 ml dimethylamine was added to it. The reaction mixture was finally cooled to −50° C.

C) Acylation:

Same procedure as in example 11 was followed. HPLC showed conversion to 70% of ceftriaxone.

Example 14

Preparation of 7-(((2-aminothiazol-4-yl)(methoxyimino)acetyl)amino)-8-oxo-3-(((1,2,5,6-tetrahydro-2-methyl-5,6-dioxo-1,2,4-triazin-3-yl) thiomethyl)-5-thia-1-azabicyclo (4.2.0) oct-2-ene-2-carboxylic acid (Ceftriaxone).

A) Activation of 2-(2-aminothiazol-4-yl)-2-syn-methoxyimino acetic acid:

8.72 g of sulfuryl chloride was slowly added to 4.7 g of dimethyl formamide at −25° C. The temperature was raised slowly to 0° C. in 60–90 minutes. Dimethyl forminium chloride chlorosulphate (DFCCS) crystallizes out at 0° C. 50 ml of dichloromethane was added to the solid crystals, which melts to get a colorless insoluble oil. This oil was decanted and taken separately. 11.37 g of 2-(2-aminothiazol-4-yl) methoxyimino acetic acid was taken in 120 ml dichlomethane and cooled to −30° C., to which the above-said oil is added. The temperature was slowly raised to −10° C. to get a clear solution and was kept at this temperature for 30 minutes.

B) Preparation of 7-amino-3-desacetoxy-3-((2,5-dihydro-6-hydroxy-3-methyl-5-oxo-as-triazin-3-yl)thio) cephalosporanic acid solution:

20.0 g of dry 7-amino-3-desacetoxy-3-(2,5-dihydro-6-hydroxy-3-methyl-5-oxo-as-triazin-3-yl thio) cephalosporanic acid was taken in 120 ml of dichloromethane to which 13.05 g of hexamethyldisilazane, 2.5 g of trimethyl chlorosilane and 0.5 g of imidazole were added and refluxed for 5–6 hours to get a hazy reaction mixture. This was cooled to 10° C. and 8.3 ml of N,N-dimethyl aniline was added and was further cooled to –50° C.

C) Acylation:

Reaction mixture A was cooled to –50° C. and reaction mixture B was added to A to get a clear solution and the resulting temperature of the reaction mixture was maintained at –45 to –50° C. for 30 minutes. HPLC monitoring showed the formation of ceftriaxone 86%.

D) Isolation:

After 30 minutes, 200 ml of water and 50 ml of triethylamine was added to get pH 6.5–7.0. The layer was separated and the aqueous layer was taken and 20 ml of isopropyl alcohol and 40 ml of ethyl acetate was added and stirred for 10 minutes at 20–25° C. pH of this aqueous layer was adjusted to 2.5 by using formic acid to get white crystals. This was further cooled to 0–5° C. and maintained for one hour. After one hour, the product was filtered and washed with 50 ml of chilled water. The product was dried under vacuum to get white crystals of purity 98%.

We claim:

1. A process for the preparation of cephalosporin antibiotics of formula II

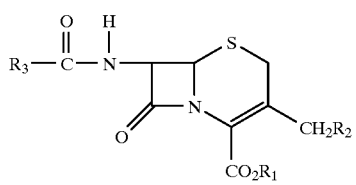

wherein $R_1$=H, carboxylic protecting group

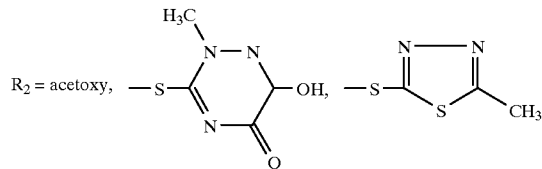

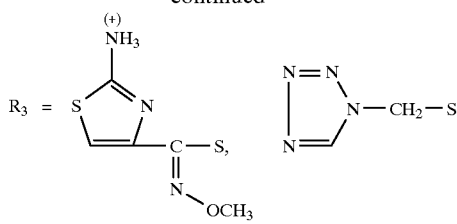

which comprises reacting silylated 7-amino cephalosporanic acid derivatives of formula X,

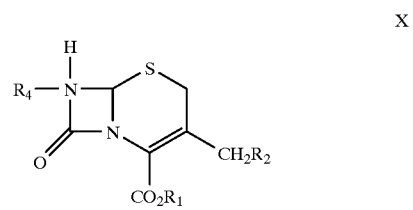

in which $R_1$, $R_2$ is as defined in said formula II; $R_4$=silyl group or hydrogen; with a reactive derivative of formula I; in a solvent such as herein described at temperature ranging from –70° C. to –30° C., preferably at about –55° C.

2. A process as claimed in claim 1, wherein the molar ratio of said reactive derivative of formula I with respect to said silylated 7-ACA is 1.1 to 2 preferably 1.2.

3. A process as claimed in claim 1 wherein said reactive derivative of formula I is 2-(2-aminothiazol-4-yl)-2-methoxyimino acetyl sulfate dimethyl dormiminium chloride according to formula Ia.

4. A process as claimed in claim 1 wherein said reactive derivative of formula I is 1H-tetrazol-1-acetyl sulfate dimethyl formiminium chloride according to formula Ib.

* * * * *